(12) United States Patent
Kamiyama

(10) Patent No.: US 6,540,676 B2
(45) Date of Patent: Apr. 1, 2003

(54) ULTRASONIC DIAGNOSTIC APPARATUS AND OPERATING SEQUENCE DETERMINING METHOD OF THE ULTRASONIC DIAGNOSTIC APPARATUS

(75) Inventor: Naohisa Kamiyama, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 09/954,189

(22) Filed: Sep. 18, 2001

(65) Prior Publication Data

US 2002/0035326 A1 Mar. 21, 2002

(30) Foreign Application Priority Data

Sep. 18, 2000 (JP) ........................................ 2000-282066

(51) Int. Cl.⁷ ................................................. A61B 8/00
(52) U.S. Cl. ........................ 600/437; 600/443; 600/458
(58) Field of Search ................................ 600/437, 443, 600/447, 454–456, 458

(56) References Cited

U.S. PATENT DOCUMENTS 5,694,937 A    12/1997   Kamiyama
5,873,829 A  * 2/1999   Kamiyama et al. ......... 600/443
6,221,020 B1 * 4/2001   Lysyansky et al. ......... 600/453

OTHER PUBLICATIONS

U.S. patent appln No. 10/191,476 filed Jul. 10, 2002.*

* cited by examiner

Primary Examiner—Francis J. Jaworski
(74) Attorney, Agent, or Firm—Oblon, Spivak, McClelland, Maier & Neustadt, P.C.

(57) ABSTRACT

An ultrasonic diagnostic apparatus for arranging functions, each of which configures a desired activity based on at least one of time information and operational information, and creating a technical flow protocol for defining work procedures in ultrasonic diagnosis is provided. Operation in scanning and in analysis processing of the ultrasonic diagnostic apparatus is controlled and executed in accordance with this technical flow protocol. In addition, in the case of reorganizing technical flow protocols in which a plurality of activities coexist, it is determined whether or not functions each configuring activities each is executable by administrating a contrast medium or medicine based on at least one of time information and operational information. In the case where it is determined that such each function is executable, a technical flow protocol is reorganized, and control in accordance with such protocol is carried out.

25 Claims, 10 Drawing Sheets

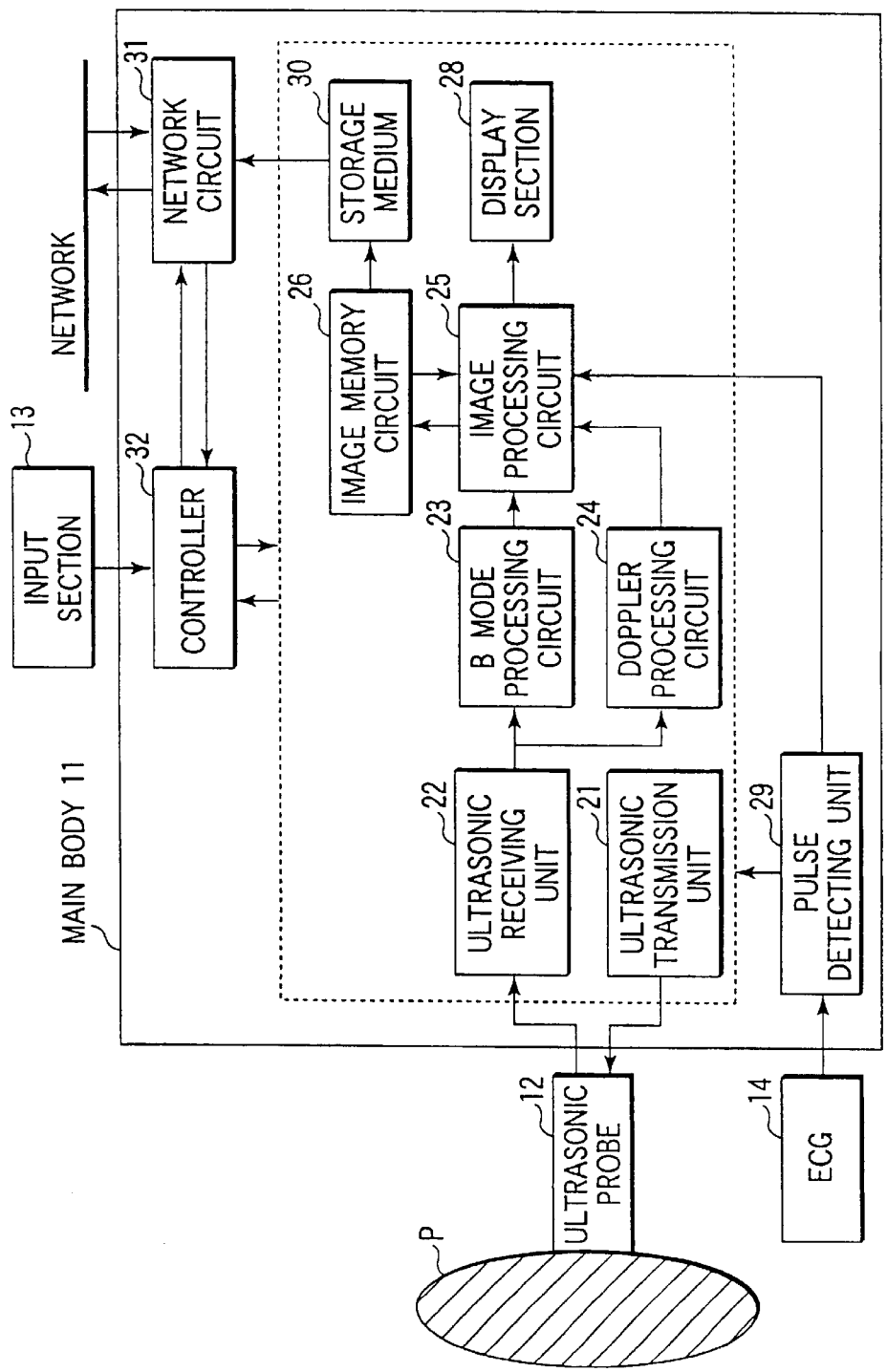
F I G. 1

ULTRASONIC DIAGNOSTIC APPARATUS AND OPERATING SEQUENCE DETERMINING METHOD OF THE ULTRASONIC DIAGNOSTIC APPARATUS

CROSS-REFERENCE TO RELATED APPLICATIONS

This application is based upon and claims the benefit of priority from the prior Japanese Patent Application No. 2000-282066, filed Sep. 18, 2000, the entire contents of which are incorporated herein by reference.

BACKGROUND OF THE INVENTION

1. Field of the Invention

The present invention relates to an ultrasonic diagnosis apparatus having an operation assistance function for an operator in a contrast medium echo technique or stress echo that is one transient diagnosis, and an operating sequence determining method of the ultrasonic diagnostic apparatus.

2. Description of the Related Art

In ultrasonic diagnosis, pulsation of a heart or movement of a fetus can be displayed in real time with simple operation in which an ultrasonic probe is applied to a body surface. In addition, because of its high safety, examination can be carried out repeatedly, and the system scale is smaller as compared with another diagnostic apparatus such as X-ray, CT or MRI, and examination can be easily carried out by moving the apparatus to a bed side. Although the scale of the ultrasonic diagnostic apparatus variously differs depending on types of functions that the apparatus comprises, a small sized ultrasonic apparatus that can be hand held by single hand has been developed. Ultrasonic diagnosis is free of being affected by x-ray exposure or the like. Thus, such ultrasonic apparatus can be used comparatively easily, and in the future, there is a possibility that a patient can operate the apparatus by oneself.

In recent years, a vein administration type ultrasonic contrast medium has been produced, and a contrast enhancement echo technique has been implemented. For example, in examination of heart, abdominal organs and the like, an ultrasonic contrast medium is administered via a vein, and a blood flow signal is enhanced for the purpose of evaluating dynamics of blood flow. In many of the contrast media, micro-bubbles become a reflection source, and a contrast enhancement effect is increased if its administration quantity/concentration is high. However, because of delicate material properties of air bubbles, it is found that such air bubbles are collapsed by ultrasonic irradiation, and a reduced time for contrast enhancement effect or the like can occur.

With respect to the contrast medium echo technique, there have been a number of researches concerning quantitative analysis technique for evaluating dynamics of blood flow as well. The most essential is so called measurement of Time Intensity Curve (TIC) for tracing a process in which an echo signal is enhanced in a region of interest after administration of a contrast medium, and graphically representing a change of its intensity with an elapse of time.

In addition, such quantitative analysis technique is applied to a stress echo technique as well. In this stress echo technique, a load is applied to the heart of a subject by administrating a medicine or exercising, thereby carrying out diagnosis or post-estimation of myocardial ischemia that could not been observed in a static state. In the case of a medicine load, the dosage of medicine is gradually increased, whereby the momentum of an exercise load, which is considered so as to avoid sudden induction of ischemia, is gradually increased for the similar reason. In such a case, the heart to which a load is applied is recovered to a static state with an elapse of time, thus making it necessary to acquire proper diagnosis data immediately after such load has been applied.

In order to carry out quantitative analysis concerning the above contract enhancement echo or stress echo, it is required to acquire data that is adaptive to elements of analysis. Ultrasonic diagnosis handles some tens of dynamic images for one second, thus requiring a large storage capacity when images of examination for about 30 minutes, for example, are recorded as digital data. In addition, even if it is possible to store a large capacity, data for use in analysis must be sampled from a large amount of recorded data, which is unavoidably cumbersome. Therefore, in actuality, there is employed a mode in which an examiner captures data required for analysis. For example, there is employed a mode in which there is recorded a dynamic image for some seconds in the vicinity where the inflow of the contrast medium into the region of interest reaches the maximum or a mode in which some typical images in the latter phase are acquired in a manner of snap pictures.

As has been described above, contrast enhancement echo or the like is a transient diagnosis including administration of medicine. Therefore, unlike a conventional examination, the region of interest cannot be observed for a long time until desired diagnosis image can be obtained. In addition, the number of administrations is generally limited to one or two. Thus, in order to carry out many analyses, it is ideal that data required for analyses of several types can be acquired at a first administration. However, in the conventional apparatus, it becomes cumbersome and difficult to execute two or more protocols for one administration.

BRIEF SUMMARY OF THE INVENTION

The present invention has been made in view of the foregoing circumstance. It is an object of the present invention to provide an ultrasonic diagnostic apparatus capable of efficiently executing a plurality of diagnosis or analysis protocols in a contrast enhancement echo or the like that is transient and that requires time management, and an operating sequence determining method of the ultrasonic diagnostic apparatus.

According to a first aspect of the present invention, there is provided an ultrasonic diagnostic apparatus comprises: a memory configured to storage a plurality of activities each of which is a function of the ultrasonic diagnostic apparatus and is added thereto first information concerning a time executable by the function in ultrasonic diagnosis and second information concerning an object of the function; a selection device configured to select an activity from the plurality of activities; a protocol creating unit configured to create work procedure protocols for arranging functions, each of which configures the selected activity in executable order, based on at least one of the first information and second information, thereby defining work procedures in ultrasonic diagnosis; a controller configured to control of the ultrasonic diagnostic apparatus based on the created work procedure protocol; and a display device configured to display the work procedures defined by the work procedure protocol as symbols.

According to a second aspect of the present invention, there is provided an ultrasonic diagnostic apparatus, comprises: a memory configured to storage a plurality of activities each of which is a function of the ultrasonic diagnostic apparatus and is added thereto first information concerning a time executable by the function in ultrasonic diagnosis and second information concerning an object of the function; a selection device configured to select at least one activity from the plurality of activities; a determining unit configured to determine whether or not functions each configuring each of the selected activities are executable, based on at least one of the first information and second information; a protocol creating unit configured to create a work procedure protocol, the protocol defining work procedures in ultrasonic diagnosis, by arranging the functions in executable order, each of the functions configuring each of the selected activities, when the determining unit determines that the functions are executable; a controller configured to control of the ultrasonic diagnostic apparatus based on the created work procedure protocol; and a display device configured to display the work procedures defined by the work procedure protocol as symbols.

According to a third aspect of the present invention, there is provided an ultrasonic diagnostic apparatus for transmitting/receiving ultrasonic waves to a subject to which a contrast medium is administered, and displaying an ultrasonic image based on the obtained ultrasonic echo, the apparatus comprises: a memory configured to storage plural types of processing protocols using a contrast medium; a selection unit configured to select a plurality of processing protocols from among the processing protocols; a scan sequence creating unit configured to create composite scan sequences obtained by combining a scan sequence that corresponds to another selected processing protocol with a scan sequence that corresponds to one selected processing protocol by the selection unit; a transmission/receiving unit configured to change sequentially ultrasonic wave transmission/receiving conditions, based on the composite scan sequences, thereby transmitting/receiving ultrasonic waves; and a generator configured to generate an ultrasonic wave image or a measurement value that corresponds to the respective processing protocols, based on the ultrasonic echo signal obtained by executing the composite scan sequences.

According to a fourth aspect of the present invention, there is provided an operating sequence determining method of an ultrasonic diagnostic apparatus, comprises: a user selecting an activity from among a plurality of activities, each of which consists of a function of the ultrasonic diagnostic apparatus, wherein there are added first information concerning a time when the function is executable in ultrasonic diagnosis and second information concerning an object of the function; and arranging functions, each of which configures the selected activity, in executable order, based on at least one of the first information and second information, thereby creating an operating sequence of the ultrasonic diagnostic apparatus.

According to a fourth aspect of the present invention, there is provided an operating sequence determining method of an ultrasonic diagnostic apparatus, comprises: a user selecting at least one activity from among a plurality of activities, each of which consists of a function of the ultrasonic diagnostic apparatus, wherein there are added first information concerning a time when the function is executable in ultrasonic diagnosis and second information concerning an object of the function; judging whether or not each function condition the each selected activity is executable based on at least one of the first information and second information; and in the case where the determining is that the each function is executable, arranging each function configuring the each selected activity in executable order, thereby creating an operating sequence of the ultrasonic diagnostic apparatus.

According to a sixth aspect of the present invention, there is provided an operating sequence determining method of an ultrasonic diagnostic apparatus, comprises: selecting a plurality of processing protocols from among plural types of processing protocols using a contrast medium; and creating composite operating sequences in which a scan sequence corresponding to another selected processing protocol is incorporated in an operating sequence corresponding to the selected processing protocol.

According to a seventh aspect of the present invention, there is provided an operating sequence determining method of an ultrasonic diagnostic apparatus, comprises: selecting a plurality protocols from among plural types of processing protocols using a contrast medium; judging whether or not the selected plurality of processing protocols are executable as a series of operating sequences; and creating composite operating sequences in which sequences each corresponding to the each selected processing protocol are combined.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram depicting an ultrasonic diagnostic apparatus according to one embodiment of the present invention;

DETAILED DESCRIPTION OF THE INVENTION

Figure 2:
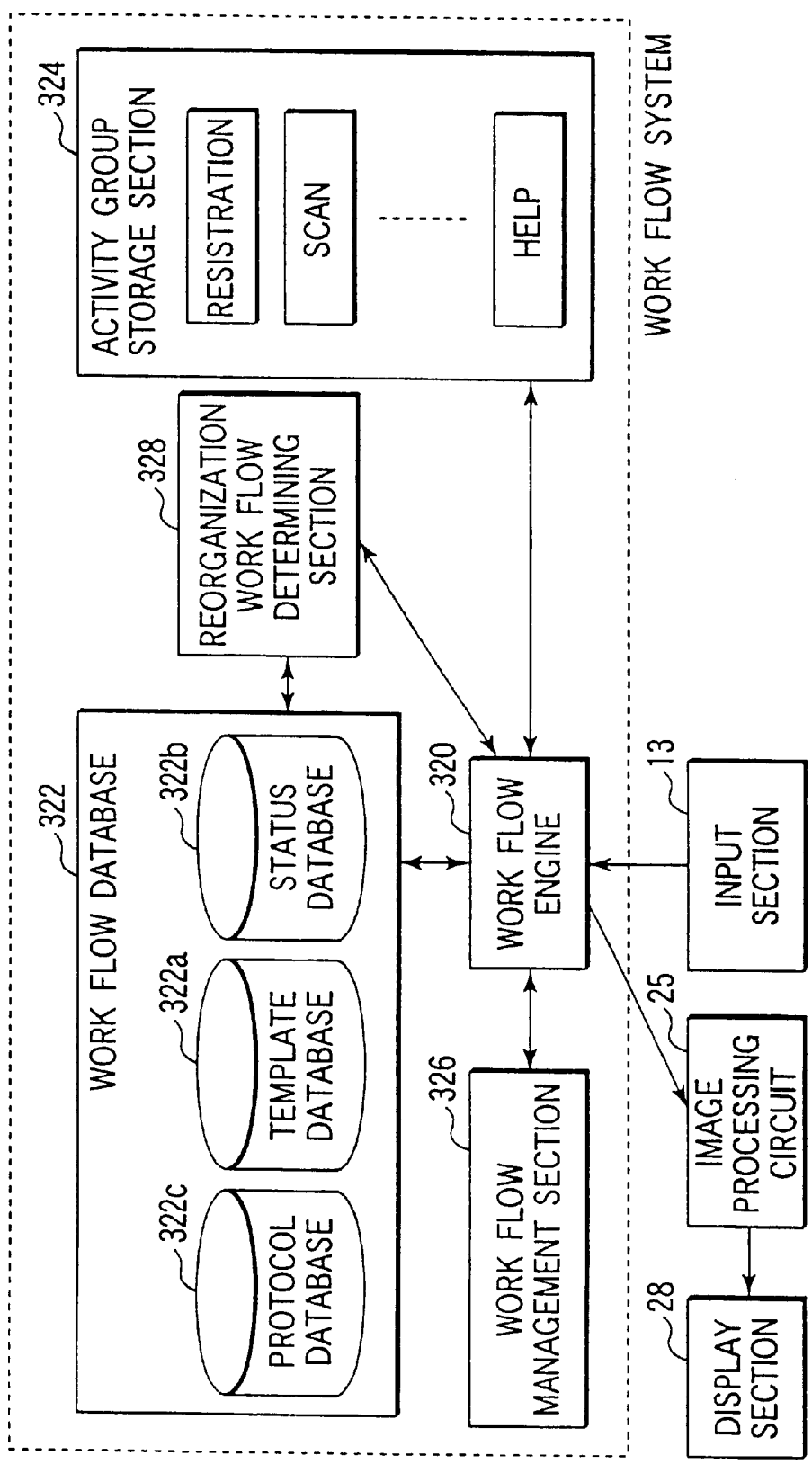
FIG. 2 is a schematic configuration of a work flow system executed by a controller 32.

Hereinafter, preferred embodiments of the present invention will be described with reference to the accompanying drawings. An ultrasonic diagnostic apparatus according to the present invention has an assistance function or the like available for executing a diagnosis protocol targeted for measurement, for example, quantitative analysis (TIC) using a contrast medium (TIC) or measurement of blood flow velocity or blood flow quantity in blood vessels or heart, or executing a diagnosis protocol in stress echo and the like. The following description will be given by way of example when a diagnosis protocol concerning quantitative analysis (TIC) using a contrast medium is executed for clarity. In the following description, constituent elements having the substantially same functions and configurations are designated by like reference numerals. A duplicate description is given only when necessary.

FIG. 1 is a block diagram depicting a schematic configuration of an ultrasonic diagnostic apparatus 10 according to the present embodiment. First, a configuration and a signal flow of the ultrasonic diagnostic apparatus 10 will be described by referring to the figure.

The ultrasonic diagnostic apparatus 10 comprises: an ultrasonic probe 12 responsible for transmitting/receiving an ultrasonic signal to/from a volunteer; a main body 11 for driving the ultrasonic probe and processing an ultrasonic probe receiving signal; an input section 13 connected to the main body and capable of inputting instruction information from an operator to the main body; and an ECG 14 for measuring electrocardiac waveforms. The input section 13 includes buttons, a keyboard, a trackball and the like, capable of controlling the diagnosis apparatus or providing a variety of image quality condition settings.

The main body 11 comprises an ultrasonic transmission unit 21, an ultrasonic diagnosis unit 22, a B mode processing circuit 23, a Doppler processing circuit 24, an image processing circuit 25, an image memory circuit 26, a display section 28, a pulse detecting unit 29, a recording medium 30, a network circuit 31, and a controller 32.

Although not shown, the ultrasonic transmission unit 21 comprises a trigger generator, a delay circuit, and a pulser circuit. This transmission unit generates ultrasonic waves, and transmits them to a vibration element of a probe 12, thereby generating convergent ultrasonic pulses. The probe 12 receives echo signals scattered in tissues in a volunteer again.

The echo signal outputted from the probe to each element is captured by an ultrasonic receiving unit 22. Although not shown, the echo signal is amplified by a pre-amplifier for each channel, and the amplified signal is A/D converted. Then, a delay time required for determining receiving directivity is assigned by a receiving delay circuit, and is added by an adder. By this addition, a reflection component from a direction according to the receiving directivity is enhanced. Comprehensive transmission/receiving ultrasonic beams are formed by the transmission directivity and receiving directivity.

An output from the ultrasonic receiving unit 22 is delivered to the B mode processing circuit 23. Here, echo signal algorithm amplification, enveloped wave detection processing or the like is applied, and data on which a signal intensity is expressed by luminance is obtained. The Doppler processing circuit 24 analyzes velocity information from an echo signal by frequency, and delivers the analysis result to the image processing circuit 25.

The image processing circuit 25 converts a scanning signal array of ultrasonic scan into a scanning signal array of a general video format represented by television. In addition, the converted signal array is composed with character information or scale for various set parameters, or alternatively, guidance image of the present invention described later, and outputs a video signal to the display section 28. Thus, a tomographic image representative of a subject's tissue morphology is displayed. In addition, the display section 28 functions as a console window to display a work flow described later as a status window, and to execute a variety of analysis programs.

In addition, the image processing circuit 25 executes graphic representation relevant to a change of intensity in a region of interest with an elapse of time, based on the inputted image signal. This graph is called TIC (Time Intensity Curve), and is used for quantitatively grasp a process in which the echo signal in the region of interest is enhanced.

The image memory circuit 26 comprises a storage memory for storing image data. This information can be called by an operator after diagnosis, for example, and dynamic image reproduction using a plurality of images can be carried out.

The storage medium 30 stores a diagnosis analysis program described later, a variety of software programs for use in work flow or the like, and a library of voices/images or the like. This storage medium is used for storing images in the image memory circuit 26. Data contained in the storage medium 30 can be transferred to external peripheral device via a network circuit 31 in a wired or wireless manner.

Physiological signal information such as electrocardiograms obtained by an ECG (electrocardiographic gating unit) 14 is converted into a digital signal by a pulse detecting unit 29. The converted digital signal is composed with a diagnostic image by the image processing circuit 25, and is displayed on a display section or is recorded in an image memory. Further, in the case where the diagnostic image is required for analysis of technical flow described later, the image is stored in the storage medium 30 or is transferred to the outside via a network circuit.

The controller 32 is control means that functions as an information processing unit (computer), and controls the entire operation of this ultrasonic diagnostic apparatus. In addition, the controller 32 executes a work flow system that is one of the essential parts of the present invention, which is described later.

Now, a work system executed in the controller 32 will be explained. The contents of work flow are described in detail in Japanese Patent Application KOKAI Publication No. 11-212157. Here, a general concept of work flow will be first described, and the features of the present invention will then be described.

The work flow system is achieved by executing a recording medium such as CD-ROM, hard disk, or memory card, or alternatively, specific work flow system software (work flow system program) supplied by a communication medium such as network.

The work flow denotes a flow of operation indicating work procedures required for predetermined diagnosis. Here, one function of the ultrasonic diagnostic apparatus is defined as a basic activity, and a series of composite functions defined by a plurality of basic activities are defined as composite activities. When work procedures required for predetermined diagnosis and analysis are defined in combination of activities, such work procedures are referred to as a work protocol. In addition, a control system of the ultrasonic diagnostic apparatus using such work flow is referred to as a "work flow system".

FIG. 2 is a schematic configuration of a work flow system executed in the controller 32. In the figure, a work flow engine 320 is drive means for causing the ultrasonic diagnostic apparatus to execute respective activities written in the work flow in specified order. A work flow database 322 comprises: a template database 322a for storing a work flow template required for driving a work flow system; a status database 322b having status information and activity information concerning the work flow stored therein; and a protocol database 322c having a work flow protocol for defining a work flow stored therein. The work flow template used here is a program concerning execution and control of activity. The status information concerning a work flow or the like is information for notifying the contents or progress of a work flow to a user or information such as start/end time.

An activity group storage section 324 is storage means for storing a program that initiate a variety of activities. Each activity program is read out and initiated by a work flow engine in accordance with a work flow order.

A work flow management section 326 displays the status of a work flow on the display window or carries out controls such as stoppage or restart of a work flow in execution according to external input.

A reorganization work flow determining section 328 is one of the features of the present invention. This section executes sequence editing based on time information concerning each processing carried out in a work flow (such as image acquisition in earlier time phase, for example), operational information (such as image acquisition based on dynamic picture or still picture, for example). That is, the reorganization work flow determining section 328 determines whether or not processings each can coexist as one ultrasonic diagnosis work without inconsistency, based on the time information or operational information assigned to each activity program. In the case where processings each are established without inconsistency, the reorganization work flow determining section 328 arranges such processings each to be coincident with each other based on each item of information, and creates a diagnosis work protocol. On the other hand, in the case where inconsistency occurs with establishment of each processing, the determining section does not create diagnosis work protocol, and notifies to an operator that such processings are not executable by using voice information or character information and the like from the display section 28.

A general work flow system includes so called patient information management such as patient data registration or attaching the diagnosis result to electronic chart.

In addition, this work flow system properly determines what the user does next, thereby making it possible to display the request message on the display section 28.

(Technical Flow)

In general, the contrast enhancement echo technique includes the following remarks. Micro-bubbles that are a main component of an ultrasonic contrast medium are easily collapsed by ultrasonic irradiation. In the contrast enhancement echo, there is designed an imaging technique that positively utilizes this collapsing phenomenon of the micro-bubbles. For example, after ultrasonic transmission has been stopped for four seconds, if the ultrasonic transmission is restarted, the contrast medium echo signal that corresponds to the blood inflow for four seconds is obtained. Further, if this stoppage intervals are changed, the time change of blood flow dynamics can be obtained. The contents of these techniques are described in detail in Japanese Patent Application KOKAI Publication No. 9-324772, for example.

Analysis utilizing the contrast enhancement echo technique is greatly associated with scan procedures (protocols) during examination. Therefore, even in the case where analysis is carried out in offline mode after examination other than analysis employing image data obtained as standard during diagnosis, it is required to determine scan protocols in advance, and to properly carry out execution of protocols and data acquisition required during diagnosis.

The important points of the present invention are to determine an analysis protocol that configures a work flow protocol and to select a scan protocol concerning the analysis protocol. Determination of this analysis protocol and selection of the scan protocol correspond to imaging and analysis in the work flow that are essential works of image diagnosis. In the following embodiment, the work defined by determination of the analysis protocol and scan protocol is referred to as a "technical flow protocol", and the flow of operation showing work procedures defined by the "technical flow protocol" is referred to as a "technical flow". Of course, in the case where general diagnosis is presumed, it is possible to include activities (such as patient registration or preparation of report) that are not associated with such technical flow.

Figure 3:
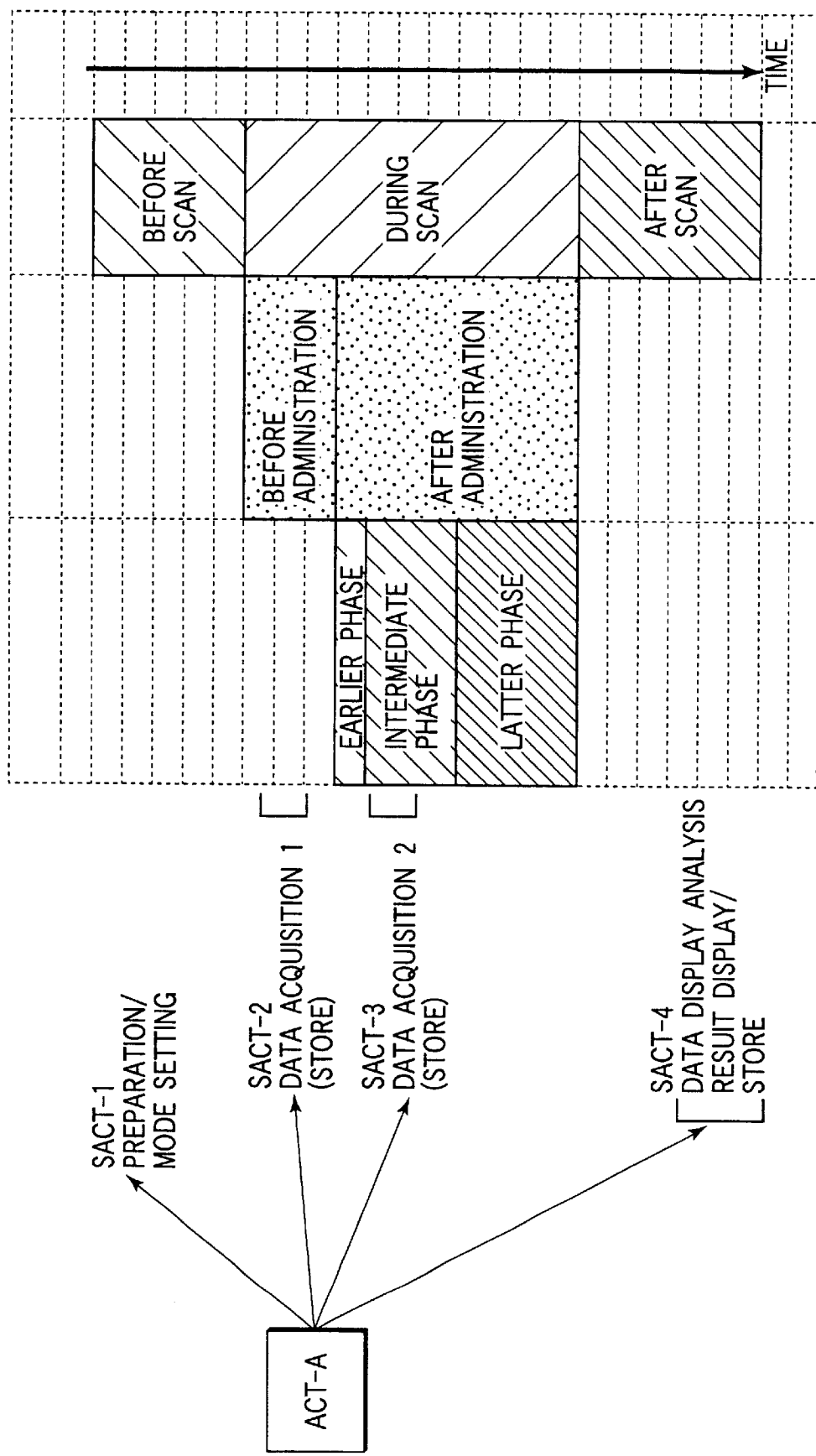
FIG. 3 is a conceptual view of one composite activity composed of a plurality of sub-activities and a view showing a relationship with an elapse of time in flow of diagnosis of sub-activities.

FIG. 3 is a view illustrating a comparatively simple example of the technical flow. As shown in FIG. 3, a protocol of one technical flow generally forms composite activities associated with every sections of an elapse of time such as pre-scanning (preparation), pre-administration and post-administration of contrast medium (earlier phase, intermediate phase, latter phase), and processing after the end of scan (analysis). The protocol of the technical flow shown in the figure corresponds to composite activities ACT-A (hereinafter, simply referred to as ACT-A) composed of a plurality of sub-activities SACT (hereinafter, simply referred to as SACT). This protocol includes a function for "comparing images before and after administration of contrast medium with each other". Each SACT includes the following functions.

A sub-activity SACT-1 (hereinafter, simply referred to as SACT-1) includes a function for image mode change optimal to analysis or condition settings such as amount of record data. A sub-activity SACT-2 (hereinafter, simply referred to as SACT-2) includes a function for acquiring an image before administration of contrast medium. A sub-activity SACT-3 (hereinafter, referred to as SACT-4) includes a function for re-displaying acquired images, and executing a comparison/analysis program. A configuration of SACT including the same function as ACT-A is not unique. For example, even if SACT-4 is configured to be further divided into sub-activities, it is possible to define the same ACT-A and achieve the same object.

Figure 4:
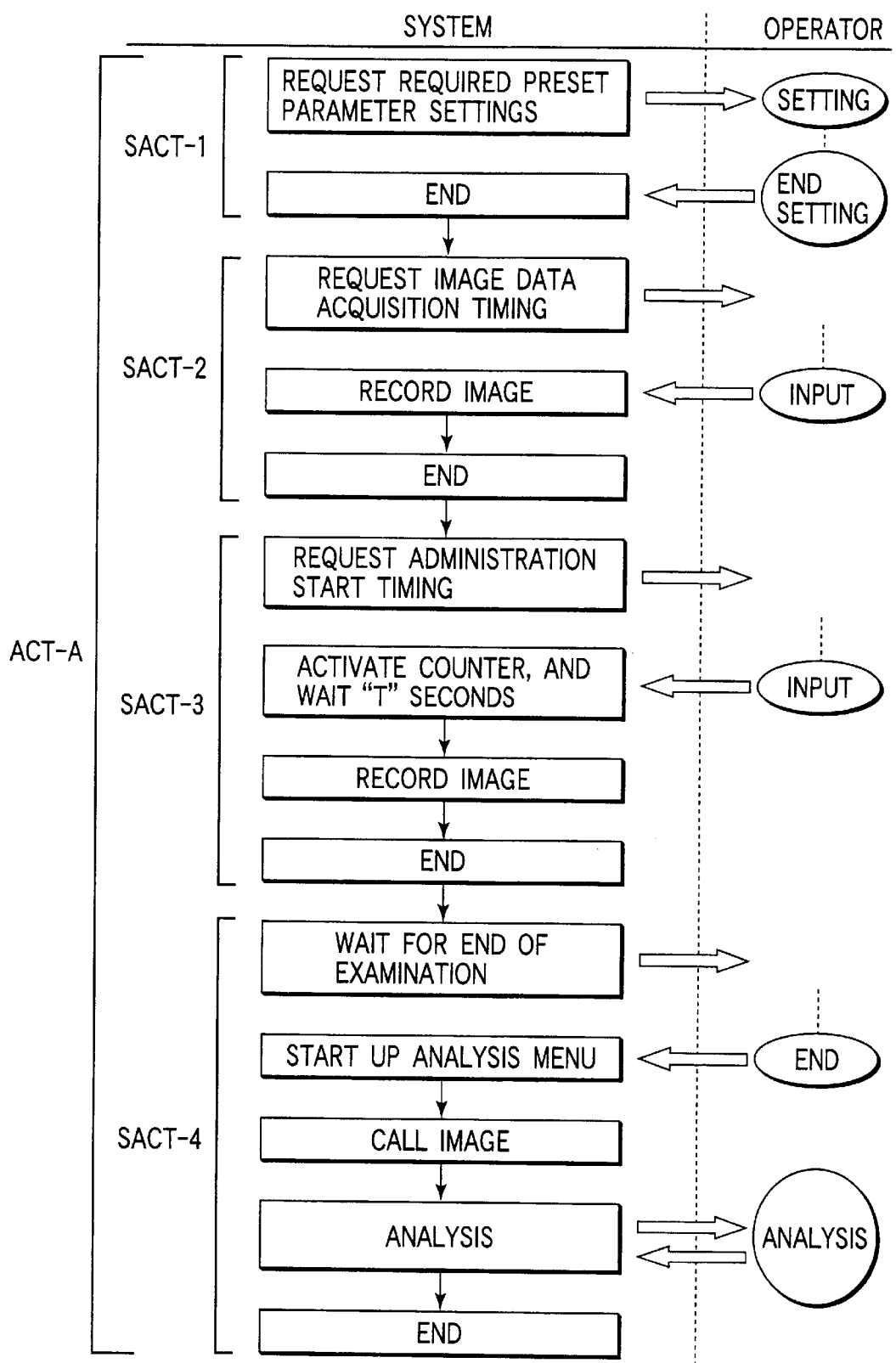
FIG. 4 is a flowchart showing specific procedures in the flow shown in FIG. 3.

Each of SACT 1 to 4 is executed as shown in FIG. 4 along an elapse of time shown in FIG. 3.

FIG. 4 shows a flow concerning system operation (user navigation and user dialogue).

In FIG. 4, when preparation before diagnosis (for example, patient ID entry) is ended by SACT-1, this system activates SACT-2, and then, displays a message for acquiring an ultrasonic image before contrast medium administration, and a button for recording an image blinks, thereby indicating the "ready" state. Then, at a timing when an operator pushed the button, image data is recorded together with an identifier indicating that "image data before contrast medium administration" is present by a desired time (number of images), and image data is recorded. At this time, as required, it is preferable to provide a configuration in which ultrasonic transmission/receiving conditions concerning acquired images (such as type of imaging mode, transmission/receiving frequency, pulse repetition frequency, frame rate, transmission sound pressure or the like) and additional physiological information described later (patient parameter information such as ECG waveform and time phase, respiratory gating information, or blood pressure) are added together with image data, and are displayed or stored.

Next, the system initiates SACT-3, and requests entry of an "administration start signal". This is because a time of about 10 to 20 seconds is generally required for administrated contrast medium to reach the region of interest, and thus, there is no change in image at an moment of an administration timing, making it difficult for the system to automatically recognize a timing of the start of administration. As in the present embodiment, there is provided a configuration in which the user is requested to enter an "administration start signal", whereby the system can determine this timing very easily.

Then, this system determine the timing, and acquires an image as follows. For example, in principle, in the case of a protocol in which image data is acquired in an intermediate phase, if there is no entry of the "administration station signal, the image is acquired in accordance with the protocol. On the other hand, as described above, in the case where there is an entry of the "administration start signal", if there is a contrast medium requiring 60 seconds from administration to sufficient circulation, for example, image acquisition is executed "after 60 seconds" when the input timing is defined as a reference. That is, this system has a function for correcting the initiation timing of each activity based on the newest information anytime with an elapse of time. A time from entry of the "administration start signal" to start of image acquisition (i.e., "after 60 seconds") can be freely changed by presetting it. In addition when information on contrast medium used in SACT-1 is inputted, there may be provided a configuration in which a program for determining an image acquisition timing is automatically selected. The system displays a message indicating that image. acquisition is in progress on the display section 28 at a time when an image acquisition timing has come, and records image data.

Another configuration makes it possible to start recording by manual operation at a user desired timing. In that case, the system requests entry of the "recording start signal" before initiating SACT-3.

When image acquisition, i.e., scanning terminates, the system determines "post-scanning (end of scan)" by recognizing procedures for returning the probe to the holder or pressing a transmission freeze button, and initiates SACT-4. Then, the system re-displays the acquired image, and a comparison/analysis program is executed.

In this work flow system described above, in the case where automatic advancement is difficult, processing is carried out interactively with a user, thereby making it possible to complete activity. The user can determine what to do next in the current protocol, making it possible to advance a protocol without any mistake even if such protocol is comparatively complicate.

Figure 5:
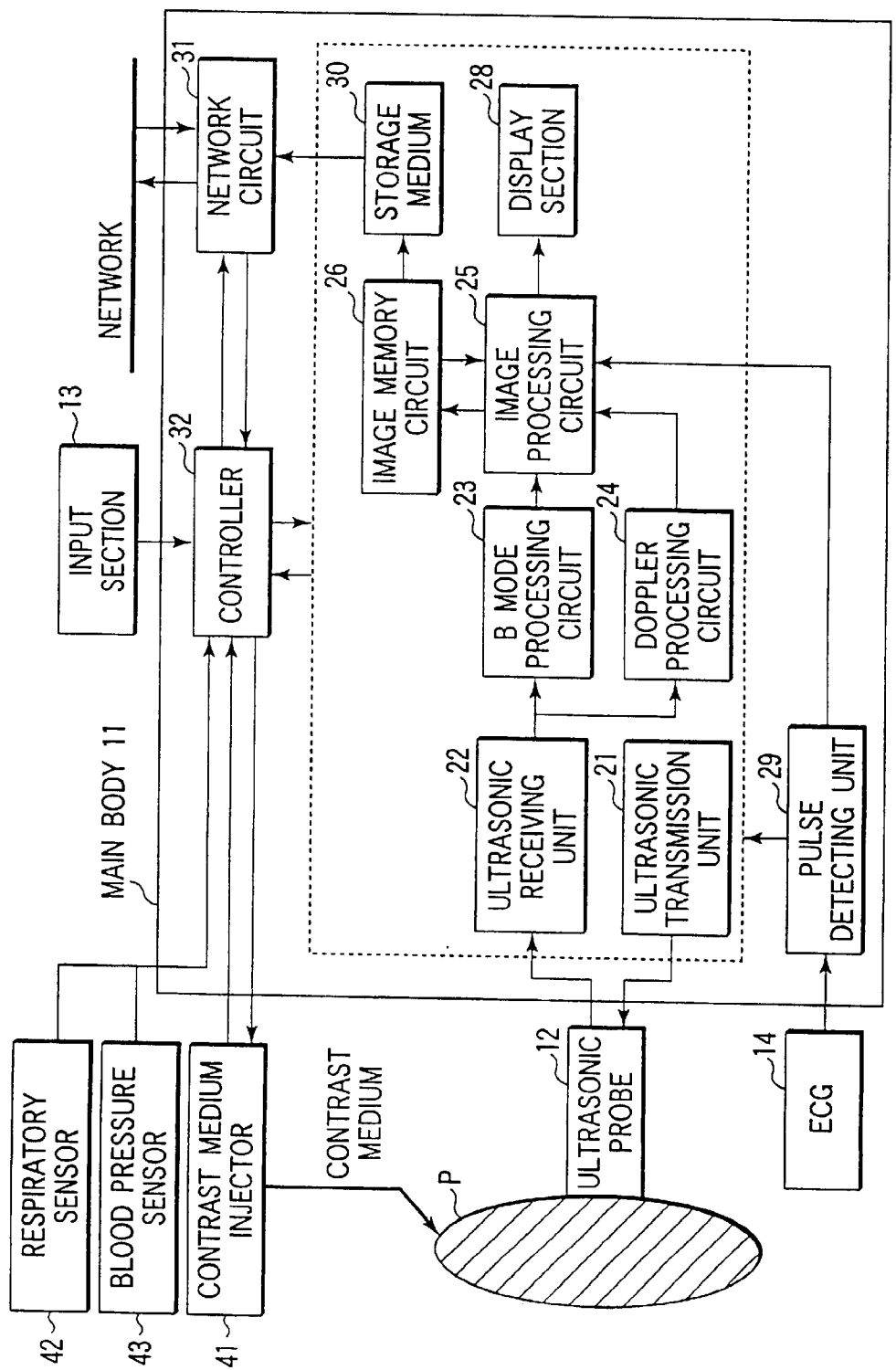
FIG. 5 is a block diagram depicting an ultrasonic diagnostic apparatus according to another embodiment of the present invention.

In addition, in this ultrasonic diagnostic apparatus, the contrast medium is placed in advance in a contrast medium injector 41 as shown in FIG. 5. The injection velocity of the contrast medium by the injector 41 is controlled by means of a controller 32. When the operator inputs an administration start button (that may be at the injector or at the input section on the system), the controller 32 controls the contrast medium injector 41 based on the input, and carries out administration at a predetermined velocity. Further, activity responsible for analysis application makes it possible to control the administration timing, injection quantity, and injection velocity of the contract medium injector 32.

Further, it is possible to connect a respiratory sensor 42 and a blood pressure sensor 43 to this ultrasonic diagnostic apparatus, as shown in FIG. 5. Physiological information concerning acquired by a variety of these peripheral devices is effective for ultrasonic diagnosis. In the system executed by this apparatus, there is provided a configuration in which the physiological information (patient parameter information such as ECG waveform and time phase, respiratory gating information, and blood pressure) is added together with image data, and is displayed or stored.

Further, according to this ultrasonic diagnostic apparatus, a user can define a acquisition mode such as B mode or Doppler mode, for example, every time phase of a scan sequence. This is accomplished by selecting an activity for carrying out scanning in a desired acquisition mode in accordance with the above technical flow. For example, in a time phase before contrast medium administration, there is no limitation to the acquisition mode. Thus, an operator can select an activity so as to monitor an image in a desired acquisition mode (such as B mode, color Doppler mode, power Doppler mode, M mode or the like). On the other hand, after contrast medium administration, activities achieving proper acquisition modes, respectively, may be selected in a variety of time phases such as an earlier phase for acquiring ultrasonic images such as vascular systems or an intermediate phase and a latter phase for acquiring ultrasonic images concerning soft tissues. Note that, the earlier phase is corresponding to the vascular phase, and the intermediate phase and a latter phase are corresponding to perfusion phase in FIG. 3.

In general, a plurality of executable technical flows are stored in the controller 32 shown in FIG. 1 in which the user merely selects a desired analysis name (or desired diagnosis technique), whereby a series of protocols required for this diagnosis/analysis is prepared.

(Second Embodiment)

A second embodiment describes an example when a plurality of technical flows are initiated in parallel to each other. That is, a work flow system according to the present embodiment includes a function for reconfiguring a scan sequence so as to enable execution in response to a user request for executing a plurality of technical flow activities, and generating new work flow protocols. Therefore, according to this work flow system, even if a protocol for executing a plurality of technical flows is planned, only one scan sequence during diagnosis is present. This sequence is created (reorganized) so that, for example, image data acquisitions exist without any duplication in a time division manner, based on the time information or operational information assigned to each activity as described later. Therefore, a plural types of diagnoses/analyses can be carried out by one execution. In the case where a plurality of sequences achieving the same advantageous effect can be defined, the operator selects them arbitrarily.

First, it is assumed that a work flow protocol for executing three types, ACT-A, ACT-B, and ACT-C, in parallel to each other is set by the operator via an edit function that this work flow system has. Then, a reorganization work flow determining section 328 edits a sequence based on the time information (such as image acquisition in earlier time phase, for example) and operational information (such as image acquisition using dynamic picture or still picture) of each processing implemented in each technical flow.

Figure 6:
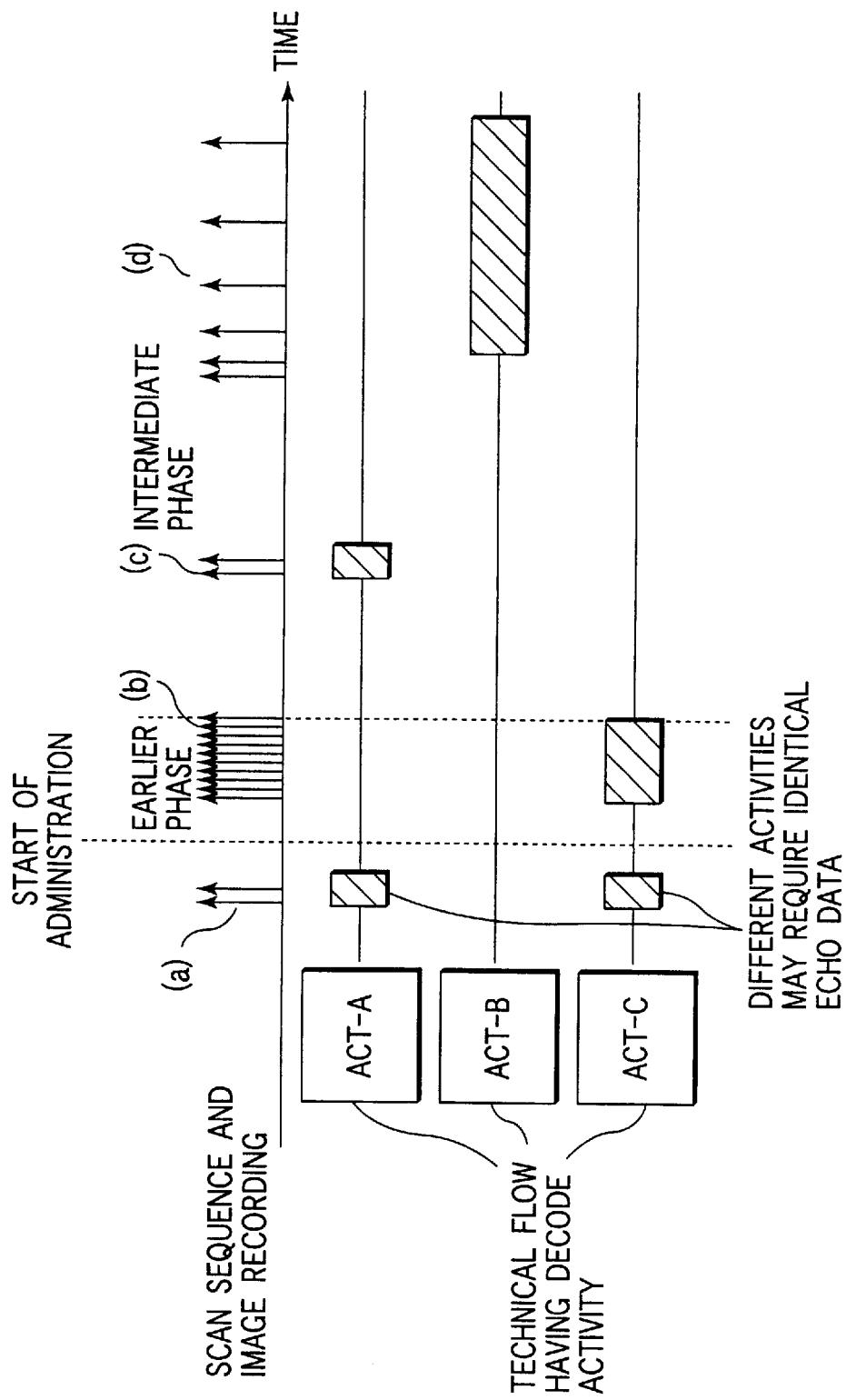
FIG. 6 is a conceptual view of a plurality of technical flow activities and the corresponding scan sequences, the figure showing an example when three different types of technical flows coexist.

FIG. 6 is a view illustrating a sequence example when three types of technical flows, ACT-A, ACT-B, and ACT-C coexist. In the figure, ACA-A executes analysis that requires still pictures (a) by several frames before administration and still pictures (c) by several frames in intermediate phase after administration. ACT-B executes analysis that requires still pictures (d) acquired while transmission intervals are changed in an intermediate phase after administration. ACT-C executes analysis that requires the still pictures (a) by several frames before administration and dynamic image data in earlier phase after administration.

The reorganization work flow determining section 328 determines a sequence as in the figure while judging that ACT-A and ACT-C are executable in the same time phase, and that no inconsistency occurs in operation mode even if these three types are executed at the same time.

Of course, there exists a technical flow that cannot coexist. For example, an earlier phase corresponds to about eight seconds after the contrast medium has reaches the region of interest. Thus, it would be difficult to execute different scan sequences in order to observe such earlier phase. In this case, the system warns the user that a technical flow cannot be selected at a stage when such technical flow is selected before diagnosis. However, as described above, in the case where ACT-A and ACT-C can use the completely identical data, they flow may coexist.

In addition, this work flow system includes a function for explicitly indicating a selectable technical flow from an inspection protocol configuration (restriction in other words) unlike the above described contents.

Figure 7:
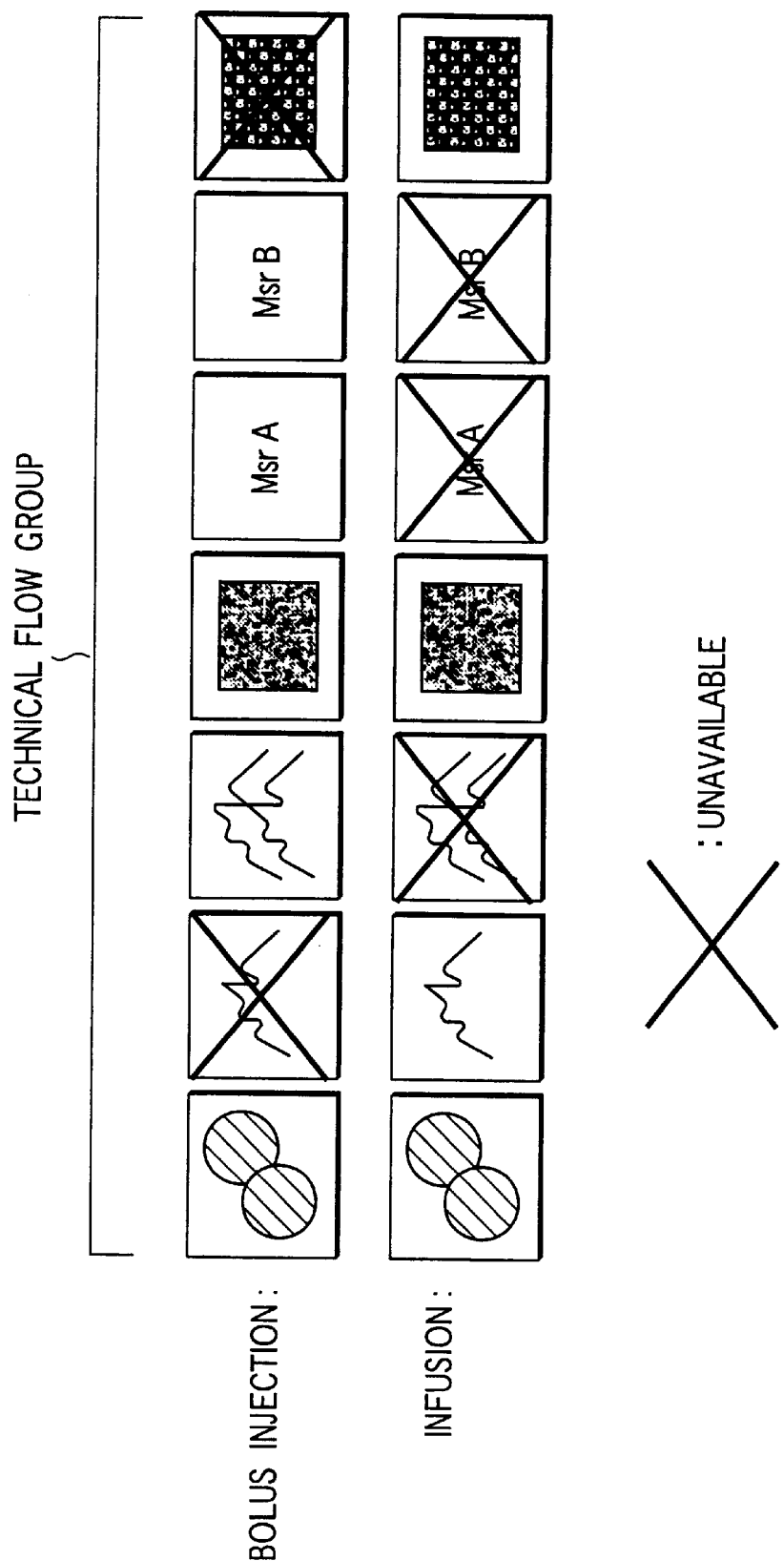
FIG. 7 is a view showing a correlation between each of preset selections and each of activities subjected to use limitation.

FIG. 7 is a view illustrating a function for explicitly indicating a selectable technical flow from an inspection protocol configuration (restriction in other words).

For example, contrast medium administration techniques include: a Bolus injection technique for administrating the medicine in the injector in batch for a short time; and an infusion technique for continuously injecting a very small amount of medicine over a long period of time by a specific injector. A certain limitation applies to the administration techniques depending on the diagnosis/analysis protocol. In this work flow system, when the user inputs an administration technique to currently executable, as shown in FIG. 7, selectable diagnosis/analysis protocols and unallowable protocols are explicitly indicated.

With such configuration, one scan sequence for executing a plurality of desired technical flows and one work flow protocol for supporting such sequence can be easily created.

Figure 8:
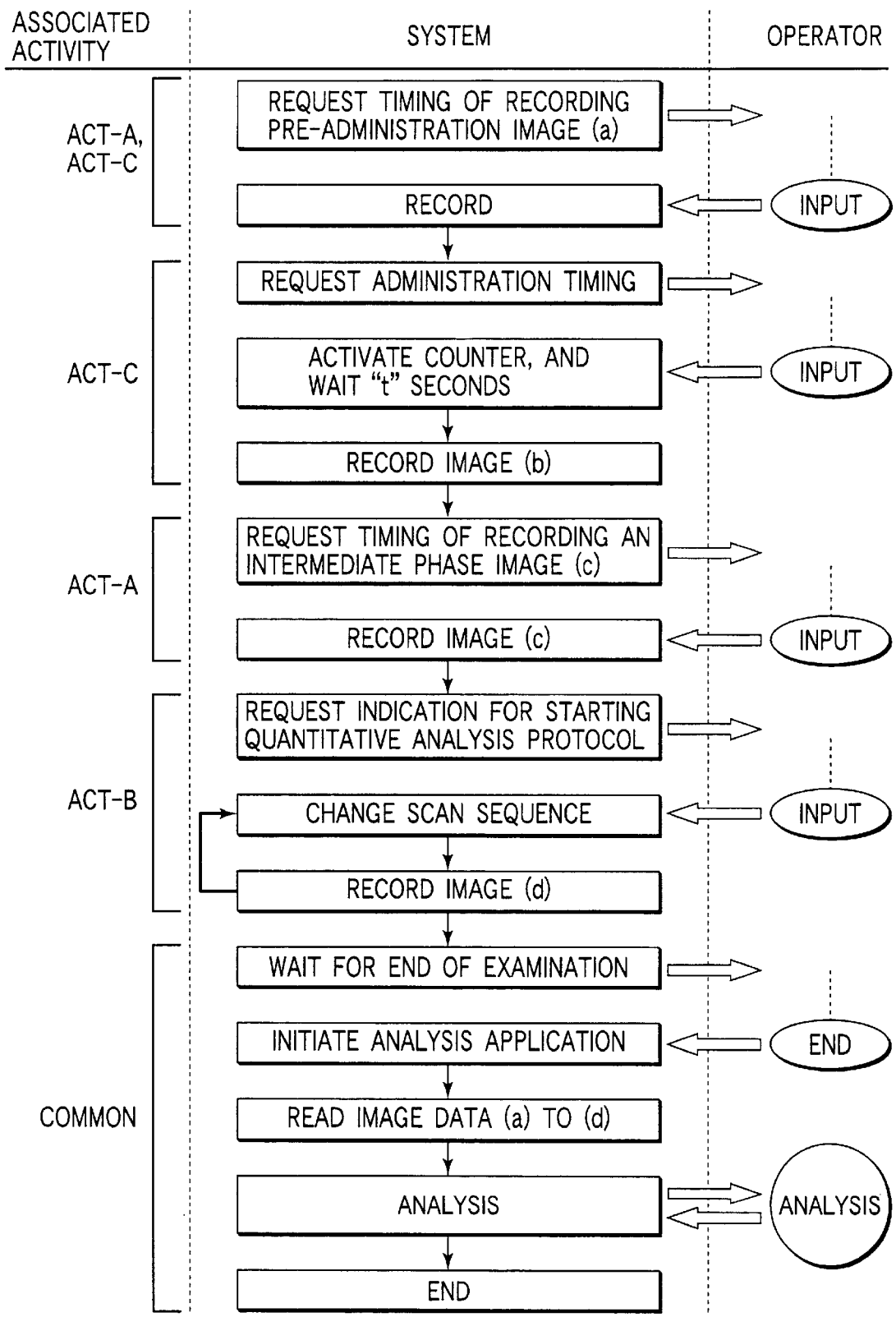
FIG. 8 is a flowchart showing specific procedures in the flow shown in FIG. 6.

A basic work for executing them is as shown in the first embodiment. FIG. 8 is a flowchart showing operations executed in accordance with the sequence shown in FIG. 6. If the system cannot make control automatically, the system acquires and records data required for analysis while recognizing a diagnosis timing by requesting the user to make entry. At this time, the data to be recorded, of course, includes patient information required for general work flow protocols and identifiers that identify data required for technical flow.

Next, a description of each section for executing diagnosis/analysis after the end of scan will be given with reference to FIG. 9.

Figure 9:
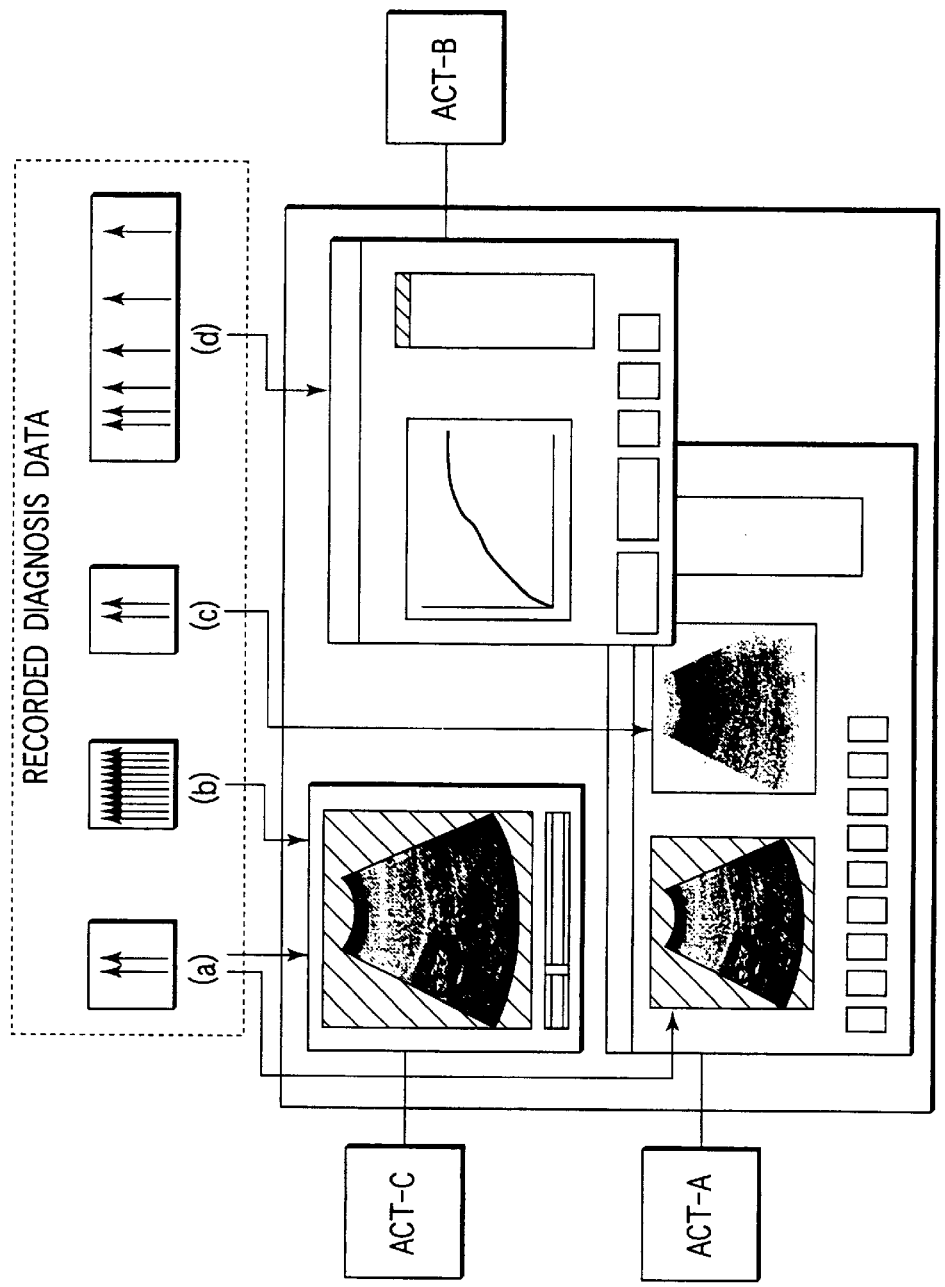
FIG. 9 shows an example of menu display while executing diagnosis/analysis that is part of technical flow activities.

FIG. 9 shows a screen of a display section 28 when a diagnosis/analysis program is initiated based on three types of technical flows shown in FIG. 6. Although three types of technical flows are set in an example shown in FIG. 6, three types of windows corresponding to them are opened in FIG. 9.

The number or shape of windows can be arbitrarily set according to type of analysis application. The recorded diagnosis data is recognized by an identifier, and is allocated on a predetermined application.

In addition, this screen may appear on a diagnosis apparatus or may appear on an external personal computer (PC). In the latter case, the required diagnosis data and analysis application program is transferred to an external device via a network circuit. Further, it is possible to initiate an application in the diagnosis system by remote operation using the external PC or the like via a network without transfer of image data.

Now, a case of executing activity that is completely different from ACT-A, ACT-B, and ACT-C at a stage when diagnosis/analysis is executed after the end of scan will be described here. This is an interrupt processing in the technical flow, and functions as a single analysis application at a stage when diagnosis/analysis is executed.

Figure 10:
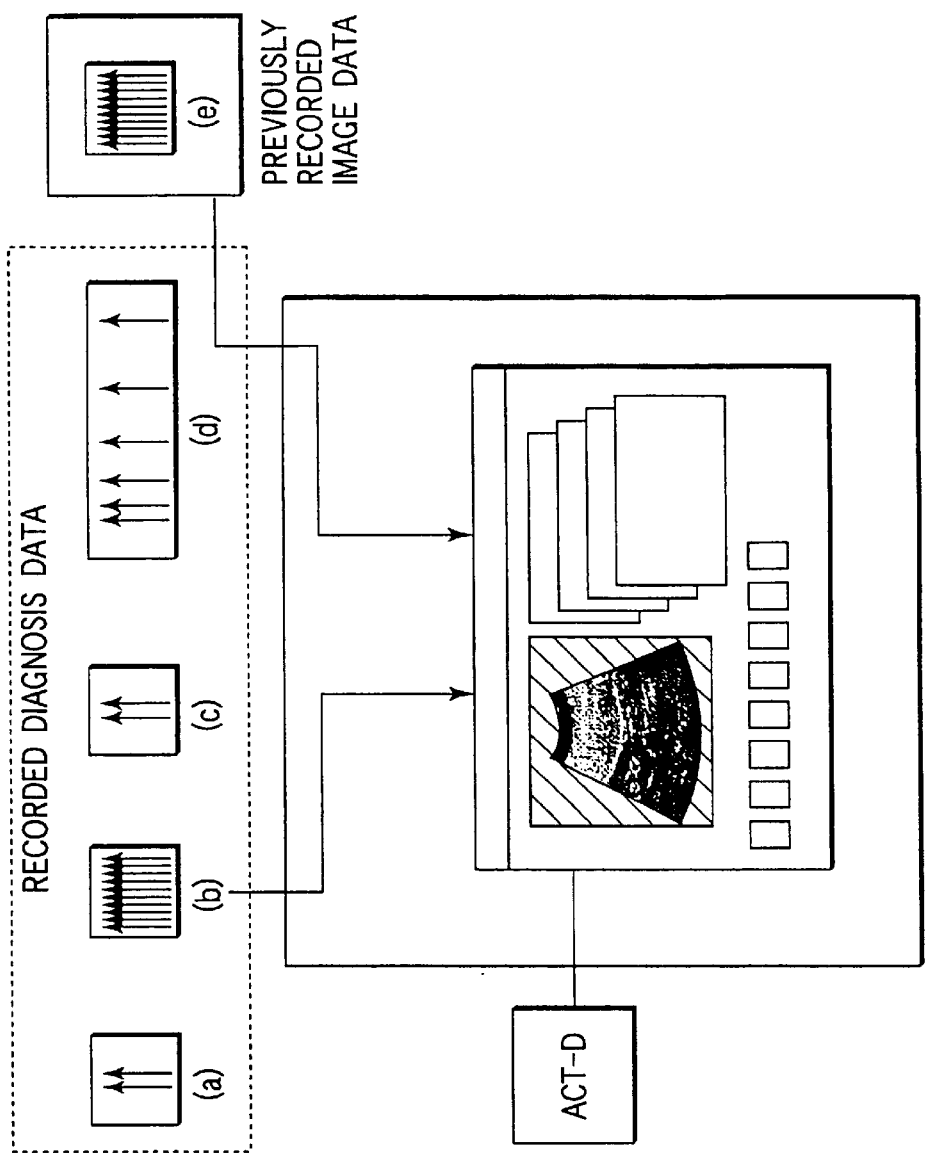
FIG. 10 is a conceptual view of diagnosis/analysis activities, each of which is activated after the end of examination.

FIG. 10 shows a screen of a display section 28 when activity "ACT-D" is initiated at a stage of diagnosis/analysis after examination.

As shown in FIG. 10, ACT-D corresponds to diagnosis/analysis activity carried out by using image (that is, image acquired by ACT-A, ACT-B, and ACT-C) shown in FIG. 9. Therefore, the data required for analysis of ACT-D is acquired by a pre-scan that is in accordance with FIG. 6, thus making it possible to initiate ACT-D after examination smoothly without any problem. In particular, simple analysis such as measurement of length and area may be executed smoothly without any problem if an image merely exists.

On the other hand, in the case where data required for analysis is deficient (for example, in the case of analysis requiring an image that cannot be acquired by ACT-A, ACT-B, and ACT-C, for example), the system warns the user that analysis is disabled.

As shown in FIG. 10, it is possible for ACT-D to call data (e) previously acquired. Further, ACT-D includes a function for using the past data stored in an internal/external storage medium according to type of technical flow.

The present embodiment shows an example of contrast enhancement echo. However, in stress echo as well, the similar technique is efficiently used. In this case, image acquisition before or after a stress has been loaded, procedures for scanning different cross sections or the like can be navigated. Of course, when contrast enhancement echo and stress echo are combined with each other, the technique of the present embodiment is effective.

With the above described configuration, the following advantageous effect can be achieved.

In transient diagnosis such as contrast enhancement echo diagnosis or stress echo diagnosis, when a comparatively complicate protocol is carried out, an interactive navigation function of the system can reduce mistakes. In particular, when it is required to acquire required diagnosis data by a specific transmission/receiving protocol, complicate user operation and mistakes caused by such operation can be reduced.

Data required for a plurality of diagnoses/analyses can be acquired by one contrast enhancement echo protocol by reconfiguring a plurality of technical flows in one sequence, thus making it possible to reduce a diagnosis time and reduce a use amount of contrast medium. As a result, medical cost can be reduced.

Although the present invention has been described above by way of embodiments, various modifications and alterations can occur to those skilled in the art within the scope of idea of the present invention, and it is construed that these modifications and alterations pertain to the scope of the present invention. For example, as in (1) and (2) shown below, various modifications can occur without departing from the spirit of the invention.

(1) In the second embodiment, there may be provided a configuration in which, after a sequence has been reorganized, this diagnosis system computes a required inspection time caused by this sequence, and notifies the computed time to an operator. Based on this computation, the operator can coordinate an examination schedule, computes an administration amount of contrast medium, and make preparations. Further, by referring to the above required time and diagnosis protocol, the system main body makes it possible to compute the administration amount or administration velocity of contrast medium and the like, and to present the operator with the amount or velocity.

(2) In the second embodiment, it is possible to execute processing by eliminating some activities from among the reorganized sequences. In this manner, there can be provided a so called rehearsal function that makes it possible to practice manipulation before a contrast medium is actually administered to a patient, for example. Although the activities targeted for such elimination specifically include indication for contrast medium injector and image recording or the like, of course, these activities can be arbitrarily selected by the operator.

The present invention is not limited to the above described embodiments, and at a stage of carrying out the invention, various modifications can occur without departing from the spirit of the invention. In addition, the above embodiments each may be carried out by properly combining them if possible, and in that case, an advantageous effect caused by such combination is achieved. Further, the above embodiments each include inventions at various stages, and such various inventions can be excerpted by using a proper combination of a plurality of constituent elements disclosed. For example, even if some constituent elements are erased from all the constituent elements shown in the embodiments, in the case where the problems described in the Description of Related Art section can be solved, and at least one of the advantageous effects described in the Detailed Description of the Invention section is achieved, a configuration having these constituent elements erased therefrom can be excerpted as the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
   a memory configured to storage a plurality of activities each of which is a function of the ultrasonic diagnostic apparatus and is added thereto first information concerning a time executable by the function in ultrasonic diagnosis and second information concerning an object of the function;
   a selection device configured to select an activity from the plurality of activities;
   a protocol creating unit configured to create work procedure protocols for arranging functions, each of which configures the selected activity in executable order, based on at least one of the first information and second information, thereby defining work procedures in ultrasonic diagnosis;
   a controller configured to control of the ultrasonic diagnostic apparatus based on the created work procedure protocol; and
   a display device configured to display the work procedures defined by the work procedure protocol as symbols.

2. An ultrasonic diagnostic apparatus, comprising:
   a memory configured to storage a plurality of activities each of which is a function of the ultrasonic diagnostic apparatus and is added thereto first information concerning a time executable by the function in ultrasonic diagnosis and second information concerning an object of the function;
   a selection device configured to select at least one activity from the plurality of activities;
   a determining unit configured to determine whether or not functions each configuring each of the selected activities are executable, based on at least one of the first information and second information;
   a protocol creating unit configured to create a work procedure protocol, the protocol defining work procedures in ultrasonic diagnosis, by arranging the functions in executable order, each of the functions configuring each of the selected activities, when said determining unit determines that the functions are executable;
   a controller configured to control of the ultrasonic diagnostic apparatus based on the created work procedure protocol; and
   a display device configured to display the work procedures defined by the work procedure protocol as symbols.

3. The ultrasonic diagnostic apparatus according to claim 1 or 2, wherein, when one of the selected activities comprises a composite activity that includes a composite function due to one combination of functions provided by the ultrasonic diagnostic apparatus, the protocol creating unit creates a work procedure protocol by arranging the functions each configuring the composite activities in executable order based on at least one of the first information and second information.

4. The ultrasonic diagnostic apparatus according to claim 1 or 2, further comprising a notification device configured to notify that the functions are not executable when the determining unit determined that the functions are not executable.

5. The ultrasonic diagnostic apparatus according to claim 4, wherein said notification device notifies an executable function or non-executable function.

6. The ultrasonic diagnostic apparatus according to claim 1 or 2, wherein said display device displays at least one of information that makes it possible to determine whether or not the diagnosis data is acquired based on any activity, ultrasonic wave transmission/receiving conditions concerning the diagnosis data, and additional information concerning a subject to the diagnosis data when diagnosis is executed in accordance with the created work procedure protocol.

7. The ultrasonic diagnostic apparatus according to claim 1 or 2, further comprising a second memory configured to storage at least one of the information that makes it possible to determine whether or not the diagnosis data is acquired based on any activity, ultrasonic wave transmission/receiving conditions concerning the diagnosis data, and additional information concerning a subject to the diagnosis data when diagnosis is executed in accordance with the created work procedure protocol.

8. The ultrasonic diagnostic apparatus according to claim 1 or 2, wherein, when a new activity is selected by the selection means while the ultrasonic diagnostic apparatus operates in accordance with the work procedure protocol, said determining unit determines whether or not the new activity is executable based on first information or second information; and when said determining unit determines that a function is executable, said protocol creating unit creates a new work procedure protocol, the new work procedure protocol defining work procedures in ultrasonic diagnosis, by arranging the functions in executable order, each of the functions configuring each of the selected new activities, when said determining unit determines that the functions are executable;

said controller controls of the ultrasonic diagnostic apparatus based on the new work procedure protocol; and said display device displays work procedures defined by the new work procedure protocol as symbols.

9. The ultrasonic diagnostic apparatus according to claim 1 or 2, further comprising a notification device configured to notify a work to be executed by the operator when a work to be done by an operator is required during execution of the work procedure protocol.

10. The ultrasonic diagnostic apparatus according to claim 9, wherein said controller executes functions at a timing at which the input is defined as a reference when an input from the operator corresponding to the notification is made.

11. The ultrasonic diagnostic apparatus according to claim 1 or 2, further comprising an analyzer configured to execute an analysis application based on acquired data.

12. The ultrasonic diagnostic apparatus according to claim 1 or 2, comprising a transmitting unit configured to transmit acquired diagnosis data and an analysis application concerning the diagnosis data to an external analysis device.

13. The ultrasonic diagnostic apparatus according to claim 1 or 2, further comprising a specification device configured to specify a desired work procedure among the work procedures defined by the work procedure protocol; wherein said controller controls said ultrasonic diagnostic apparatus based on a work procedure protocol from which the specified work is omitted or a work procedure protocol for executing only the specified work.

14. The ultrasonic diagnosis apparatus according to claim 1 or 2, further comprising a notification device configured to calculate a time required for completion of the created work procedure protocol and notify the time.

15. The ultrasonic diagnostic apparatus according to claim 1 or 2, further comprising:

a second determining unit configured to determine at least one of an administration quantity of a contrast medium required for the ultrasonic diagnosis and an administration velocity based on the any required time; and wherein said notification device notifies the administration quantity of the contrast medium or the administration velocity of the contrast medium to an operator.

16. An ultrasonic diagnostic apparatus for transmitting/receiving ultrasonic waves to a subject to which a contrast medium is administered, and displaying an ultrasonic image based on the obtained ultrasonic echo, the apparatus comprising:

a memory configured to storage plural types of processing protocols using a contrast medium;

a selection unit configured to select a plurality of processing protocols from among the processing protocols;

a scan sequence creating unit configured to create composite scan sequences obtained by combining a scan sequence that corresponds to another selected processing protocol with a scan sequence that corresponds to one selected processing protocol by said selection unit;

a transmission/receiving unit configured to change sequentially ultrasonic wave transmission/receiving conditions, based on the composite scan sequences, thereby transmitting/receiving ultrasonic waves; and a generator configured to generate an ultrasonic wave image or a measurement value that corresponds to the respective processing protocols, based on the ultrasonic echo signal obtained by executing the composite scan sequences.

17. The ultrasonic diagnostic apparatus according to claim 16, wherein the composite scan sequences are configured so that a scan sequence time is shorter than a case in which selected processing sequences are individually executed.

18. The ultrasonic diagnostic apparatus according to claim 16, wherein the composite scan sequences are configured so that an administration quantity of a contrast medium is smaller than a case in which the selected processing sequences are individually executed.

19. An ultrasonic diagnostic apparatus for transmitting/receiving ultrasonic waves to a subject to which a contrast medium is administered, and displaying ultrasonic images based on the obtained ultrasonic echo, the apparatus comprising:

a memory configured to storage plural types of processing protocols using a contrast medium;

a selection unit configured to select a plurality of processing protocols from among the processing protocols;

a determining unit configured to determine whether or not the plurality of processing protocols selected by said selection unit are executable at the same time;

a transmission/receiving unit configured to change sequentially ultrasonic wave transmission/receiving conditions, based on a composite scan sequence according to the processing protocols selected by said selection unit, thereby transmitting/receiving ultrasonic waves; and a creating unit configured to create an ultrasonic image or a measurement value that corresponds to the respective processing protocols, based on the ultrasonic echo signal obtained by executing the composite scan sequence.

20. The ultrasonic diagnostic apparatus according to claim 19, further comprising a acquisition mode determining unit configured to determine a acquisition mode for said ultrasonic diagnostic apparatus according to a time phase of the composite scan sequence.

21. An operating sequence determining method of an ultrasonic diagnostic apparatus, comprising:

a user selecting an activity from among a plurality of activities, each of which consists of a function of the ultrasonic diagnostic apparatus, wherein there are added first information concerning a time when the function is executable in ultrasonic diagnosis and second information concerning an object of the function; and arranging functions, each of which configures the selected activity, in executable order, based on at least one of the first information and second information, thereby creating an operating sequence of the ultrasonic diagnostic apparatus.

22. An operating sequence determining method of an ultrasonic diagnostic apparatus, comprising:
- a user selecting at least one activity from among a plurality of activities, each of which consists of a function of the ultrasonic diagnostic apparatus, wherein there are added first information concerning a time when the function is executable in ultrasonic diagnosis and second information concerning an object of the function;
- determining whether or not each function condition the each selected activity is executable based on at least one of the first information and second information; and
- in the case where the determining is that the each function is executable, arranging each function configuring the each selected activity in executable order, thereby creating an operating sequence of the ultrasonic diagnostic apparatus.

23. An operating sequence determining method of an ultrasonic diagnostic apparatus, comprising
- selecting a plurality of processing protocols for different diagnoses/analyses from among plural processing protocols using a contrast medium; and
- creating a composite operating sequence by combining operating sequences corresponding to the selected plurality of processing protocols.

24. An operating sequence determining method of an ultrasonic diagnostic apparatus, comprising:
- selecting a plurality protocols from among plural types of processing protocols using a contrast medium;
- judging whether or not the selected plurality of processing protocols are executable as a series of operating sequences; and
- creating composite operating sequences in which sequences each corresponding to the each selected processing protocol are combined.

25. The operating sequence determining method according to claim 24, further comprising defining a acquisition mode of the ultrasonic diagnostic apparatus in accordance with a time phase of the composite operating sequence.

* * * * *